(12) United States Patent
Hansson et al.

(10) Patent No.: US 9,867,412 B2
(45) Date of Patent: Jan. 16, 2018

(54) GARMENT COMPRISING CHASSIS AND BELT

(75) Inventors: Roy Hansson, Gothenburg (SE); Niklas Svensson, Hisings Backa (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 865 days.

(21) Appl. No.: 14/362,607

(22) PCT Filed: Dec. 9, 2011

(86) PCT No.: PCT/SE2011/051495
§ 371 (c)(1),
(2), (4) Date: Jun. 4, 2014

(87) PCT Pub. No.: WO2013/085445
PCT Pub. Date: Jun. 13, 2013

(65) Prior Publication Data
US 2014/0345034 A1    Nov. 27, 2014

(51) Int. Cl.
*A61F 13/15*    (2006.01)
*A61F 13/20*    (2006.01)
(Continued)

(52) U.S. Cl.
CPC .............. *A41F 1/00* (2013.01); *A61F 13/64* (2013.01)

(58) Field of Classification Search
CPC .................................. A41F 1/00; A61F 13/64
See application file for complete search history.

(56) References Cited

U.S. PATENT DOCUMENTS 5,135,522 A   8/1992   Fahrenkrug et al.
5,549,593 A   8/1996   Ygge et al.
(Continued)

FOREIGN PATENT DOCUMENTS

CN    1048798 A    1/1991
CN    101172075 A    5/2008
(Continued)

OTHER PUBLICATIONS

Extended European Search Report dated Aug. 24, 2015, issued in corresponding European Patent Application No. 11877071.8 (6 pages).
(Continued)

*Primary Examiner* — Michele M Kidwell
(74) *Attorney, Agent, or Firm* — Drinker Biddle & Reath LLP

(57) ABSTRACT

An article includes a chassis and a belt to be placed around the waist of a wearer and separable from the chassis. A front and/or rear portion of the chassis includes a pair of first fasteners detachably attachable to the outer surface of the belt and separated by a first distance. The chassis includes a pair of first stretch markings related to the first distance. The belt includes a pair of second stretch markings marking a second distance when in a relaxed state and a predetermined third distance when in a stretched state. In a relaxed state, the first stretch markings are positioned in conjunction with or within the second stretch markings allowing the chassis to be attached to the belt in the relaxed state via the first fasteners and allowing the belt to be stretched into the third distance without jeopardizing the fastening of the first fasteners.

16 Claims, 6 Drawing Sheets

(51) Int. Cl.
*A41F 1/00* (2006.01)
*A61F 13/64* (2006.01)

(56) References Cited

U.S. PATENT DOCUMENTS

| | | | |
|---|---|---|---|
| 5,906,604 A | 5/1999 | Ronnberg et al. | |
| 5,971,970 A | 10/1999 | Carlbark et al. | |
| 6,336,922 B1 * | 1/2002 | VanGompel | A61F 13/49466 604/385.29 |
| 6,478,787 B1 | 11/2002 | Ihrfelt et al. | |
| 7,211,072 B2 * | 5/2007 | Nawata | A61F 13/505 604/353 |
| 8,251,968 B2 * | 8/2012 | Fernfors | A61F 13/64 604/386 |
| 2006/0068168 A1 | 3/2006 | Olson et al. | |
| 2008/0312632 A1 | 12/2008 | Fernfors | |
| 2009/0182298 A1 | 7/2009 | Kumasaka | |
| 2009/0182299 A1 * | 7/2009 | Brinkdopke | A61F 13/64 604/391 |

FOREIGN PATENT DOCUMENTS

| | | | |
|---|---|---|---|
| CN | 101854899 A | | 10/2010 |
| EP | 0 409 307 A2 | | 1/1991 |
| EP | 409307 B1 | | 9/1996 |
| EP | 648482 B1 | | 3/2001 |
| JP | 2010082139 A | | 4/2010 |
| JP | 2011030604 A | | 2/2011 |
| JP | 5033750 B2 | | 9/2012 |
| RU | 2312648 C2 | | 12/2007 |
| WO | WO-9614815 A1 | | 5/1996 |
| WO | WO-9907319 A1 | | 2/1999 |
| WO | WO 03/082168 | | 10/2003 |
| WO | WO-2005053588 A1 | | 6/2005 |
| WO | WO-2006068541 A1 | | 6/2006 |
| WO | WO-2009043101 A1 | | 4/2009 |
| WO | WO 2009/082290 A1 | | 7/2009 |

OTHER PUBLICATIONS

Chinese Office Action dated Feb. 4, 2015 issued in corresponding Chinese patent application No. 201180075386.7 (22 pages including English translation).

Decision on Grant dated Aug. 3, 2015 issued in corresponding Russian patent application No. 2014127890 (9 pages) (6 pages English language translation).

* cited by examiner

GARMENT COMPRISING CHASSIS AND BELT

CROSS-REFERENCE TO PRIOR APPLICATION

This application is a §371 National Stage Application of PCT International Application No. PCT/SE2011/051495 filed Dec. 9, 2011, which is incorporated herein in its entirety.

TECHNICAL FIELD

The disclosure relates to an article including a chassis and a belt. The belt can be separated from the chassis and arranged to be placed around the waist of a wearer. The belt includes an inner surface facing the user during use and an outer surface facing away from the user during use. The belt includes first elastic means for allowing stretching of the belt during use in a lateral direction. The chassis includes at least a first layer of a conformable material for the user. The chassis includes longitudinal sides and lateral sides and is divided into a front portion, a rear portion and a crotch portion located between the front portion and the rear portion in a longitudinal direction. The front portion and/or the rear portion of the chassis includes a pair of first fastening means being separated by a first distance. The chassis is arranged to be detachably attached to the outer surface of the belt by means of said first fastening means. The outer surface includes second fastening means arranged to be detachably attached to the first fastening means.

BACKGROUND

Articles in the shape of pants are known from many examples in the art. Some of these articles are provided with a belt arranged to be placed around the waist of a wearer in order to facilitate putting the article on or off. Some articles have a belt that is integrated with a chassis, where the belt is discarded together with the chassis. Alternatively the belt may form a separate part detachably attached to the chassis. See U.S. Pat. No. 5,971,970 and U.S. Pat. No. 5,906,604 for prior art articles.

In the case of a detachable belt the belt is provided with attaching elements, which are attached to each other when the belt is placed around the waist of the wearer in use. To put the chassis on, the wearer attaches one of the ends of the chassis to the belt. The free end of the chassis is then passed through between the legs of the wearer and attached to the belt.

A problem with existing articles is that there is a risk that the chassis will detach from the belt if the belt is elongated more than the maximum possible elongation of the material between the attachment elements of the chassis. By attaching the chassis to the belt and thereafter stretching the belt there is a possibility that the elongation of the elastics in the chassis will reach a maximum limit before the elastics of the belt reaches its maximum elongation. The result may then be that the attaching elements may separate from the belt if elongated further due to stress from the elongation of the belt. This may result in the article becoming misplaced on the user, thereby resulting in reduced functionality of the article or that the chassis simply falls off. In the case where the article is an absorbent article, this may lead to unwanted soiling of garments and similar.

SUMMARY

In view of prior art there is a need for an improved article that remedies the above mentioned problems.

It is desired to provide an article that overcomes the issue of a chassis that involuntarily detaches from a belt.

The disclosure relates to an article including a chassis and a belt. The belt is separate from the chassis and is arranged to be placed around the waist of a wearer. The belt includes an inner surface facing the user during use and an outer surface facing away from the user during use. The belt includes first elastic means for allowing stretching of the belt during use in a lateral direction. The chassis includes at least a first layer of a conformable material for the user. The chassis includes longitudinal sides and lateral sides and is divided into a front portion, a rear portion and a crotch portion located between the front portion and the rear portion in a longitudinal direction. The front portion or the rear portion of the chassis includes a pair of first fastening means being separate with a first distance. The chassis is arranged to be detachably attached to the outer surface of the belt by means of said first fastening means. Said outer surface includes second fastening means arranged to be detachably attached to the first fastening means. The chassis includes a pair of first stretch markings being related to the first distance. The belt includes a pair of second stretch markings marking out a second distance when the belt is in a relaxed state and a predetermined third distance when the belt is in a stretched state. The first stretch markings are intended, in the relaxed state, to be positioned in conjunction with the second stretch markings or within the second distance for allowing the chassis to be attached to the belt in the relaxed state via the first fastening means and allowing the belt to be stretched into the third distance without jeopardizing the fastening of the first fastening means.

By having first stretch markings on the chassis and second stretch markings on the belt marking out when the belt is in a relaxed or a stretched state, the problem of attaching the chassis to the belt and being able to stretch the belt farther than the elastic of the chassis allows is avoided.

When attaching the chassis, which normally has none or a lower degree of elongation capacity than the belt, the user attaches the chassis so that its stretch markings are aligned with the second stretch markings or within the second distance. In the relaxed state, that part of the chassis being attached to the belt will "hang loose" in the first fastening means. Here "hang loose" means that the portion between the first fastening means is unstretched and can be folded, crumbled, hang in a curvature, or the like. The first distance is measured along the curvature or path of the chassis which means that when the belt is stretched to its maximum, corresponding to the third distance, the chassis lies flush against the belt, but in the relaxed state the distance between the first fastening means measured along the belt is less than the distance between the first fastening means when measured along the chassis. This ensures that when the belt is stretched/elasticated partly or fully to the predetermined third distance, the loose chassis portion becomes less loose than in the relaxed state, but never so extended (non-elastic chassis) or stretched (elastic chassis) that the predetermined distance between the first fastening means is exceeded. Hence, the risk of the belt being separated from the chassis is removed or at least radically reduced.

Furthermore, this also allows for the chassis to be safely attached to the belt either when the belt is already positioned on the user, i.e. in an elongated state, or when the chassis is attached to the belt before the article is put on a user.

The first stretch markings may be positioned in conjunction with the first fastening means. However, the stretch markings may be placed anywhere on the chassis, provided there is a separation between them and that they are arranged on the front and/or rear portion of the chassis and that the relationship between the stretch markings are considered for the first distance. The relationship should be such that the maximum allowable distance between the first fastening means are considered in view of the predetermined maximum stretch of the belt according to the above. During positioning of the first stretch markings onto the belt, focus may be put on the fastening means in order to ensure that they are attached properly. An advantage of having the stretch markings placed in conjunction with the first fastening means is to reduce the area of focus for the person putting the chassis into place. There is no need for the person to first ensure that the first stretch markings are in the correct place before switching to attach the first fastening means to the belt. The positioning and fastening may be done in one fluent motion.

The distance between the first stretch markings may be greater than the second distance in the relaxed state. The distance between the first stretch markings may essentially be equal to or greater than the third distance in the stretched state. A distance between the first stretch markings greater than the second distance of the belt in the relaxed state allows the caretaker or user to pre-stretch the belt up to a distance equal to the difference of the distance between the first stretch markings and the second distance prior to putting on the chassis without jeopardizing the fastening of the first fastening means. Further, having the distance between the first stretch markings equal to or greater than the third distance in the stretched state allows for an even safer way of pre-stretching the belt prior to putting on the chassis without jeopardizing the fastening of the first fastening means.

The second distance may be dependent on the stretchability of the first elastic means. Having different elastics in the belt makes it possible to vary the stretchability of the first elastic means. Having different degrees of stretchability in the belt allows the belt to be stretched to different degrees of elongation. Varying the second distance simplifies the putting on of the article in that the second distance is adapted for a pre-determined stretchability.

The chassis may include second elastic means, wherein the first stretch markings marks out a fourth distance when the chassis is in a predetermined maximum stretched state, wherein the fourth distance is essentially equal to or greater than the third distance in the stretched state. The chassis may include elastic means in order to allow the chassis to elongate as well as the belt. By having second elastic means in the chassis, the chassis may more easily conform to the stretching of the belt, thereby further insuring that the first fastening means stay in place. By having elastic means in the chassis the comfort of the article may also be increased as the fit of the chassis may improve.

The third distance may relate to a predetermined maximum stretch value of the belt in the stretched state.

The belt may include a stretch zone, wherein the distance between the outer boundaries of the stretch zone when elongated to its maximum is less than or equal to the distance between the first stretch markings in said chassis when the chassis is stretched out to its maximum.

The belt may be completely elastic or only partly elastic. The stretchability of the elastic may be such that the belt, between its second stretch markings, can be elongated less than the chassis, between its first stretch markings, when both the belt and the chassis are maximally elongated. This would further reduce the risk of jeopardizing the fastening of the first fastening means.

The distance between the outer boundaries of the stretch zone on the belt when elongated to its maximum is less than or equal to the distance between the first stretch markings on the said chassis, when the chassis is stretched out to 90% of its maximum, or to 80% of its maximum.

By allowing the second distance to never exceed more than 80-90% of the maximum chassis elongation, the chassis elastic may never reach their maximum elongation as the belt is elongated. This eliminates the risk of the chassis to be elongated beyond its maximum whereupon the first fastening means would risk de-attachment from the belt.

The stretch zone of the belt may include an elastic means sandwiched between two essentially non-elastic members. This is one way of constructing the belt. The belt may of course include more than one stretch zone.

The stretch zone on the belt includes a coloured region. The advantage of this is to further simplify the attachment of the chassis by visualising the zone where the belt is elongated.

The stretch zone on the belt includes ink added to the surface of the material which is placed away from the user's body.

The chassis is made from a washable material. This enables the reuse of the chassis, thereby providing a more economical and environmentally friendly article. The belt may of course also be washable in order for the complete article to be reusable.

The chassis may include a top sheet, a back sheet and an absorbent core placed in-between the top sheet and the back sheet.

The article may be used as an absorbent article. An absorbent package including an absorbent core placed between a top sheet and a back sheet may be incorporated with the chassis or may be placed as an insert in the chassis. The article may also be used for other purposes using other kinds of insert or be used as a kind of garment.

The first fastening means may include hook material and the second fastening means may include loop material, or vice versa.

The entire belt may be elasticated.

The first stretch marking on the chassis may include two transversal extending marks separated from each other. Other kinds of marks are of course conceivable. The chassis may also include a coloured region between the first stretch markings or have other kinds of marks in the shape of geometrical figures or other motifs.

It should be noted that the predetermined maximum stretch of the material, could refer to when the material is stretched until it is dumb.

DETAILED DESCRIPTION OF DRAWINGS

Figure 1:
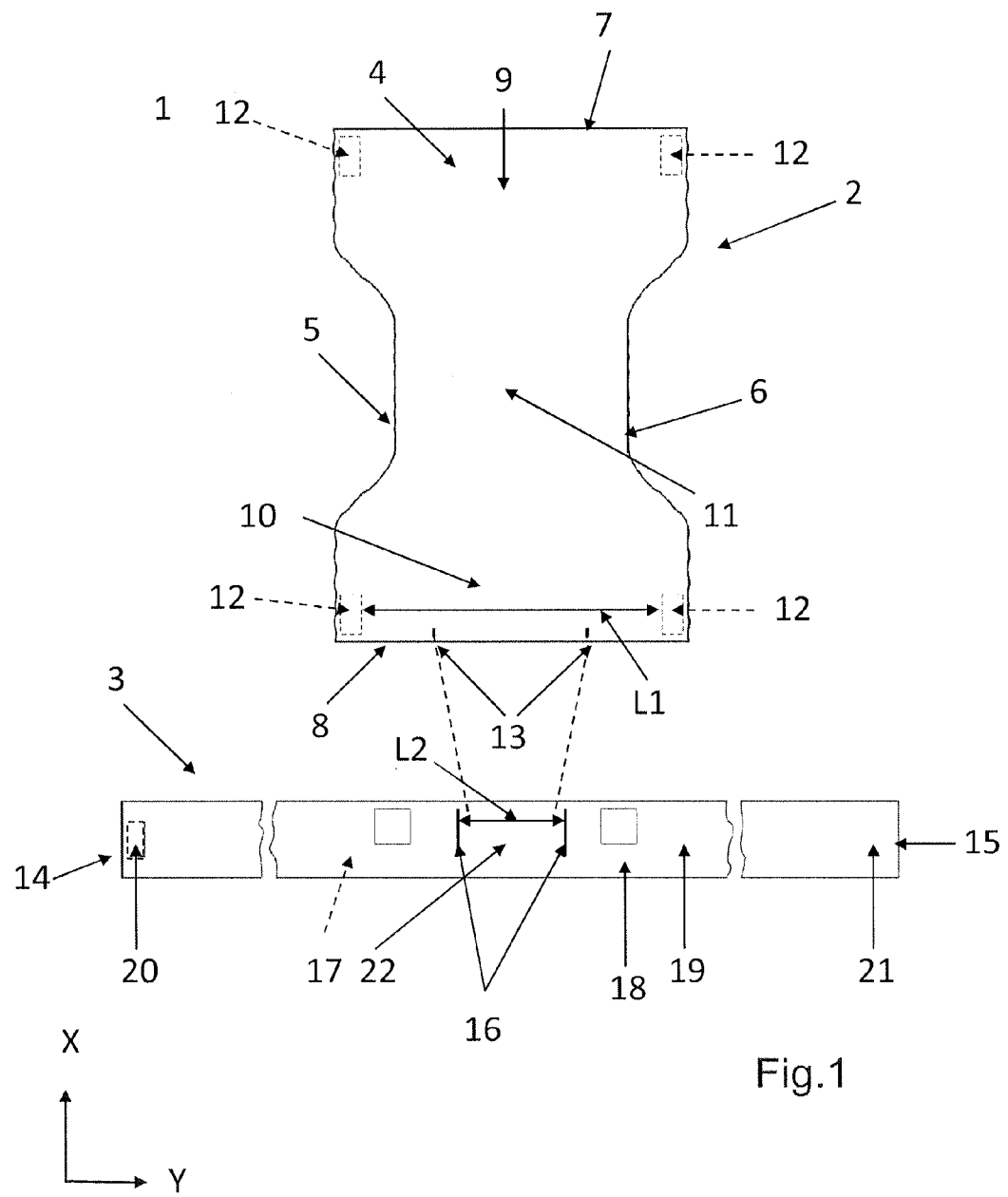
FIG. 1 schematically shows an article including chassis and belt according to a first aspect, FIG. 2 schematically shows an article including chassis and belt according to a second aspect, FIG. 3 schematically shows an article including chassis and belt according to a third aspect, FIG. 4 schematically shows an article including chassis and belt according to a fourth aspect, FIG. 5 schematically shows a chassis according to a fifth aspect.

FIG. 1 schematically shows an article 1 including a chassis 2 and a belt 3 according to a first aspect. The chassis 1 in FIG. 1 is seen from the side facing away from a wearer.

The chassis 2 includes at least a first layer 4. In certain embodiments, the first layer 4 is a conformable material for the user. Examples of liquid permeable materials are non-woven, perforated plastic films, plastic or textile web and water permeable foam materials. Water permeable materials that are constituted by thin continuous fibres that have an elongation essentially in the longitudinal or lateral direction of the article can also be used. The chassis can also be a laminate of two or more of the abovementioned materials. Also, the chassis can be formed of combinations of different materials in different regions of the article. The chassis may be constructed to support a separate absorbent core (not shown in FIG. 1) or to have an absorbent core placed between a top sheet and a back sheet. In case of a separate core, the core is placed into the chassis 2 either directly on top of a surface facing the user or in a pocket designed to hold an absorbent core. A chassis having an absorbent core placed between a top sheet and a back sheet will be described in more detail below.

The chassis 2 may also include a laminate of two or more layers. In some embodiments, the material or materials making up the chassis 2 are washable in order for the chassis 2 to be used more than once.

The chassis 2 extends along its longitudinal direction X and lateral direction Y. The chassis 2 further includes a first longitudinal side 5, a second longitudinal side 6, a first lateral side 7 and second lateral side 8. The chassis 2 is divided into a front portion 9 and a rear portion 10 with a crotch portion 11 located between the front portion 9 and the rear portion 10 in a longitudinal direction. In FIG. 1, the rear portion 10 includes first fastening means 12 in order for the chassis to be detachably attached to the belt. FIG. 1 shows that the rear portion 10 includes the first fastening means 12. The first fastening means 12 are separated by a first distance L1. The chassis 2 may be longitudinally symmetrical and laterally symmetrical such that the chassis 2 can be attached to the belt 3 at the front portion 9 and/or the rear portion 10.

Figure 2:
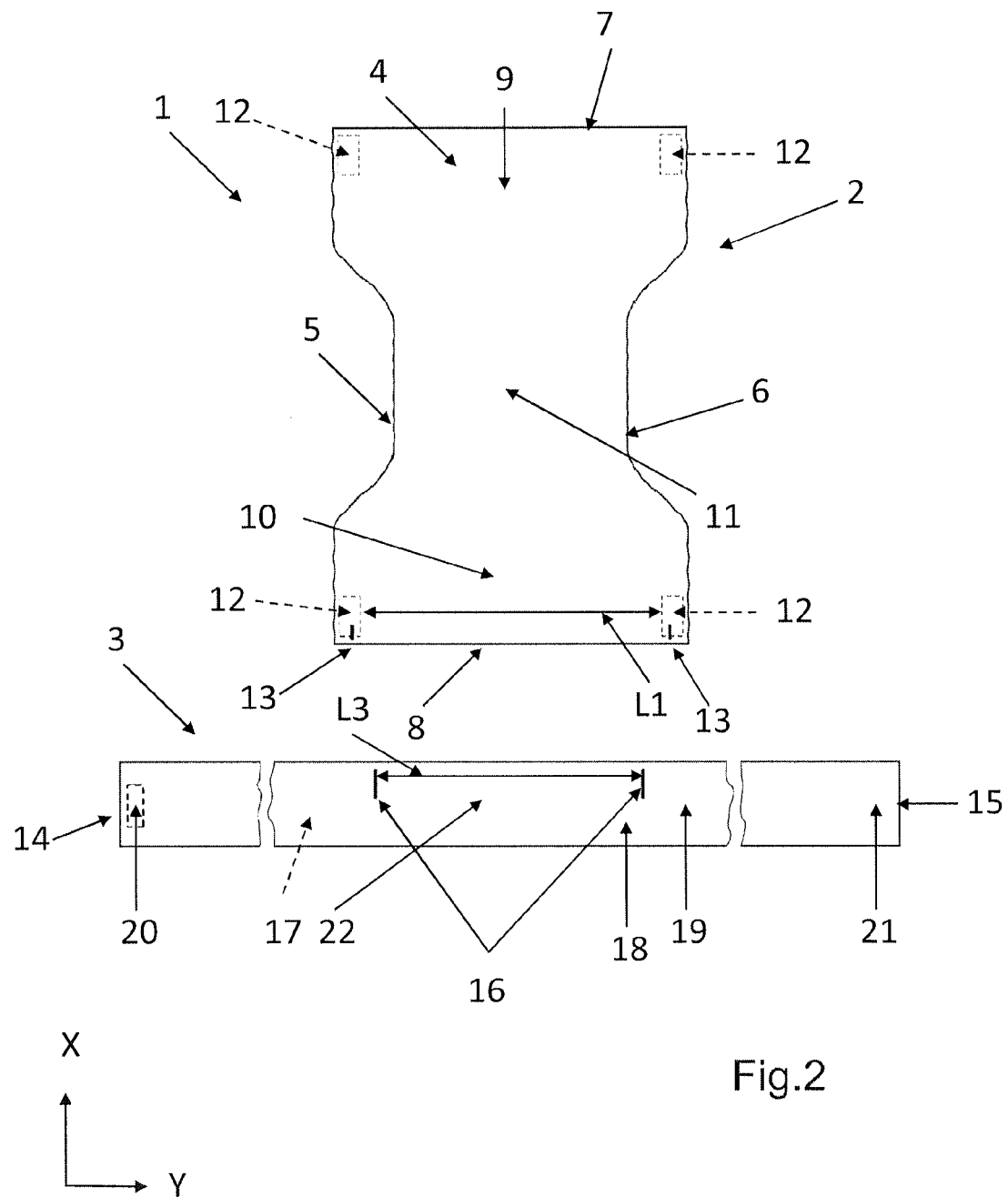
Figure 3:
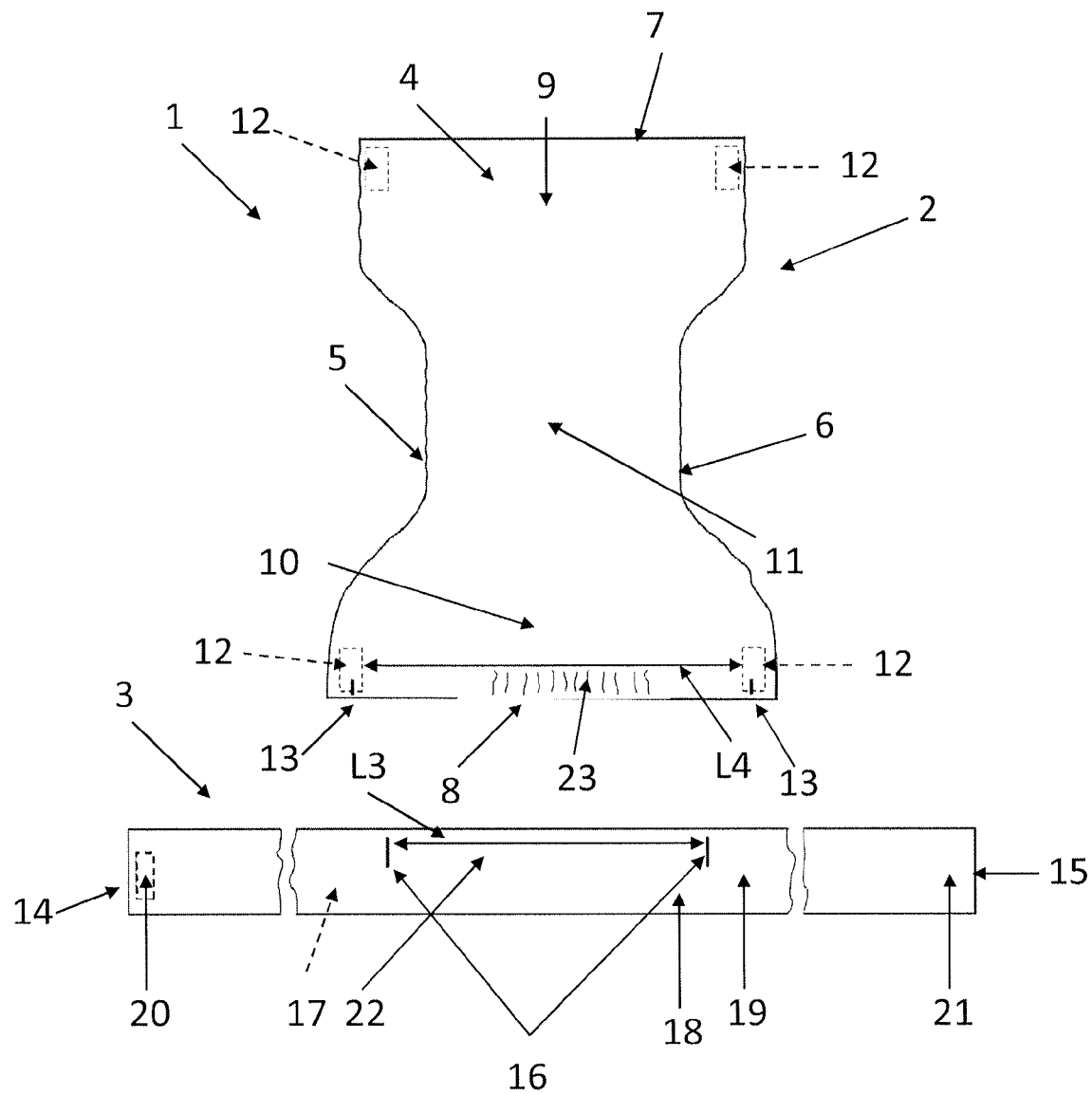

The chassis 2 includes first stretch markings 13. In FIG. 1, a pair of stretch markings are used. More than two stretch markings can be used as first stretch markings 13. The first stretch markings 13 are positioned along the first lateral side 7 and/or the second lateral side 8 of the chassis 2 in a lateral direction. The first stretch markings 13 are placed in relation to the first distance L1. This means that the first stretch markings 13 are always placed at a specific distance from the first fastening means 12. This specific distance may be dependent on various parameters, for example the flexibility of the chassis, but the main purpose is to either directly or indirectly mark the position of the first fastening means 12. If the specific distance is zero, then the first stretch markings 13 are positioned at the same position as the first fastening means 12 and thereby directly marks the position of the first fastening means 12. When the specific distance is zero, the distance between the first stretch markings 13 are equal to the first distance L1. This is illustrated in FIGS. 2 and 3. The first fastening means 12 may constitute the first stretch markings 13. The first fastening means 12 and the first stretch markings 13 may be coloured in different colours. The first stretch markings may include at least two longitudinally extending marks separated from each other or at least two laterally extending marks separated from each other or two diagonally extending marks. Other shapes of stretch markings are possible such as arrows, triangles, circles, curvatures or other suitable geometric or pictorial shapes.

The belt 3 in FIG. 1 is shown in parts illustrating that the belt may be made in different lengths and the length of the belt 3 does not have to be related to the size of the lateral sides 7, 8 of the chassis 2. The belt 3 includes a first end 14 and a second end 15. The belt 3 includes second stretch markings 16 marking out a second distance L2 when the belt is in the relaxed state. FIG. 1 shows two broken lines marking that the first stretch markings 13 on the chassis should be placed inside the second distance L2, but may be positioned in conjunction with or on the second stretch markings. The first distance L1 is taken along the chassis and gives enough slack for the chassis, when being attached to the belt and being in a non-stretched state, such that the belt can be stretched such that the slack is reduced but not to the extent that the stretched length of the belt is greater than the first distance L1. This means that the correlation between the first stretch markings 13 and the first attachment means 12 gives the possibility to arrange the second stretch markings 16 on the belt dependent on the features of the belt 3, i.e. e.g. stretchability, in such a way that the first stretch markings 13 can be positioned on the second stretch markings 16 or within the second distance L2 and then attaching the first fastening means 12 to the belt 3 without jeopardizing that the first fastening means 12 becomes un-attached when the belt is stretched.

The belt 3 further includes an inner surface 17 facing the user during use and an outer surface 18 facing away from the user during use. The outer surface 18 of the belt includes second fastening means 19 arranged to cooperate with the first fastening means 12 in order for the chassis to be detachably attached to the belt. The first fastening means 12 of the chassis 2 and the second fastening means 19 of the belt will be explained, by way of example, based on the hook and loop connection between the chassis 2 and the belt 3 by means of hook elements and loop elements. It should be understood that the hook and loop connection is just for illustration, not limitation to the present invention. In fact, the hook elements may be replaced by adhesive strips while the corresponding loop elements may be replaced by landing surfaces which are attachable to the adhesive strips. It is possible to position the hook element on the chassis 2 and the loop element on the belt 3 or vice versa.

In certain embodiments, the hook material can be a "Moulded Hook Fastener" from Velcro called "ULTRA-MATE HTH847®" (see, e.g., http://www.fasteningsystems.com/ultra_mate_hth_hook.html). Such hooks have a "palm tree shape" (see, e.g., http://www.velcro.com/index.php?page=business-products-all-ultra-mate), and the hook density is 140±14 hooks/cm$^2$. The belt material (loop material) may be a laminate including a loop layer and a support layer. The loop layer can be included on the outer surface 18 of the belt 3. One example of a loop layer is a 30 g/m$^2$ carded nonwoven, 2.2 dtex, 100% PP fibres supplied by Fiberweb Tenotex. The exemplary carded loop layer is bonded with a Tric Trac pattern. The exemplary carded loop layer further includes a support layer oriented toward the wearer made of spun bond, 100% PP fibres, with a surface weight of 50 g/m$^2$. As illustrated, the support layer forms the inner surface 17. The two layers constituting the exemplary laminate are ultrasonic point bonded together, with approximately 4 mm between points. As an alternative to the above description, the belt 3 may be formed by nonwoven materials as a loop material, so as to use the belt itself as loop elements.

The belt 3 further includes third fastening means 20 arranged at the first end 14 of the belt and fourth fastening means 21 arranged at the second end 15 of the belt 3. The third and fourth fastening means 20, 21 are intended to secure the belt 3 around the waist of a wearer. The third and fourth fastening means 20, 21 may be of the same kind as described for the first and second fastening means 12, 19; or the third and fourth fastening means 20, 21 may be different from the first and second fastening means 12, 19. The entire outer surface of the belt 3 may be covered with loop material, wherein the second fastening means 19 and the fourth fastening 21 means may be made from the same loop material.

The belt 3 includes first elastic means 22 for allowing stretching of the belt during use in a lateral direction. As stated above, the belt 3 may be a laminate formed by at least two layers. The wearer facing layer of the belt 3, also referred to as "support layer", should be soft, non-irritating and comfortable against the skin. The garment facing layer of the belt, i.e., outermost layer, is of non-woven materials. The outermost layer itself may be used as a unitary loop element and is bonded to the supporting layer by any means known in the art such as ultrasonic welding, thermal welding, adhesive bonding etc. Both the layer facing the wearer and the layer facing the garment may be made of a nonwoven material. The first elastic means may be sandwiched in between the two layers in the laminate. The belt may also be constructed such that the belt includes just a single layer of material. In this case the first elastic means 22 are attached to the outer surface 18 of the belt 3. The first elastic means may be elastic threads, elastic foam, elastic laminate or web. In FIG. 1, the belt 3 is elasticated along the entire length of the belt. It is possible to only elasticate part of the belt 3 as described below.

It should be noted that the front portion 9 is also equipped with fastening means 12 and that the first stretch markings 13 could be positioned in the front portion and in connection to the fastening means 12 in a corresponding manner to what has been described in connection to the back portion 10. Furthermore, both the front and back portion could be equipped with the first stretch markings 13.

FIG. 2 schematically shows an article 1 including a chassis 2 and a belt 3 according to a second aspect. The difference between the chassis described in FIG. 1 and the chassis described in FIG. 2 is that the first stretch markings 13 are placed essentially in conjunction with the first fastening means 12. FIG. 2 also shows the belt in a stretched state and the second stretch markings 16 now marks out a third distance L3 between themselves.

Regardless of the position of the first stretch markings 13, the first stretch markings 13 are positioned on or inside the second stretch markings 16 when the belt 3 is in a relaxed or stretched state. Furthermore, in the relaxed state the distance between the first stretch markings 13 are greater than the second distance L2 and in the maximum stretched state the distance between the first stretch markings 13 are equal to or greater than the third distance L3. This causes the belt 3, when it contracts back to its relaxed state, to slightly crumple the front portion 9 and/or rear portion 10 of the chassis 2 that is attached to the belt 3. When the belt 3 is stretched to a stretched state the front portion 9 and/or rear portion 10 of the chassis 2 that is attached to the belt 3 will then return to an essentially plane state.

FIG. 3 schematically shows an article 1 including a chassis 2 and a belt 3 according to a third aspect. In FIG. 3, the first stretch markings 13 are positioned in the same position as the first fastening means 12 in the same way as depicted in FIG. 2. However, the example described in connection to FIG. 3 could also refer to a chassis having the first stretch markings 13 positioned according to FIG. 1. In FIG. 3, the belt 3 is stretched out to its maximum elongation. This means that the distance L3 has reached its predetermined maximum length.

Except for the position of the first stretch markings 13, the difference between FIGS. 1 and 2 is that the chassis 2 in FIG. 3 includes second elastic means 23 located along the front and/or rear portion 10, in other words described as waist elastic. The second elastic means 23 may be elastic wire, cord, strip, thread, etc, interposed between a top sheet and a back sheet of the chassis by sewing, gluing, thermal welding, etc, so that the top sheet and back sheet are pleated when the waist elastic is relaxed. Alternatively, the second elastic means 23 may also be non-elastic nonwoven materials which is stretched or necked elasticized, or may be elastic laminate formed by laminating an elastic layer and a non-elastic layer. Although the second elastic means 23 is described above as an integral part of the chassis 2 between a top sheet and a back sheet, it may also be an elongate waist elastic produced separately and then attached to the chassis at one or both lateral sides 7, 8 thereof by means, such as sewing, thermal welding, etc. with two attaching elements provided in the two ends of the separated waist elastic.

In FIG. 3, the second elastic means 23 of the chassis 2 is stretched out. This results in the distance L1 being increased and the distance between the first stretch markings 13 being increased accordingly. When the second elastic means 23 are stretched to its maximum, the distance between the first stretch markings mark out a fourth distance L4. The fourth distance L4 is essentially equal to or greater than the third distance L3 of the belt 3 in its maximum stretched state. In FIG. 3, the distance between the first fastening means 12 are indicated as stretched out to their maximum distance L4.

In FIG. 3, the first stretch markings 13 are placed on or inside the second stretch markings 16 indicating that the maximum elongation of the belt 3 coincides with a predetermined elongation of the chassis 2. The first stretch markings 13 and the second stretch markings may also be arranged such that they are in line when both the chassis 2 and the belt 3 are stretched out to their respective maximum elongation.

The second elastics 23 described in FIG. 3 could be used on the chassis described in connection to FIGS. 1 and 2.

Figure 4:
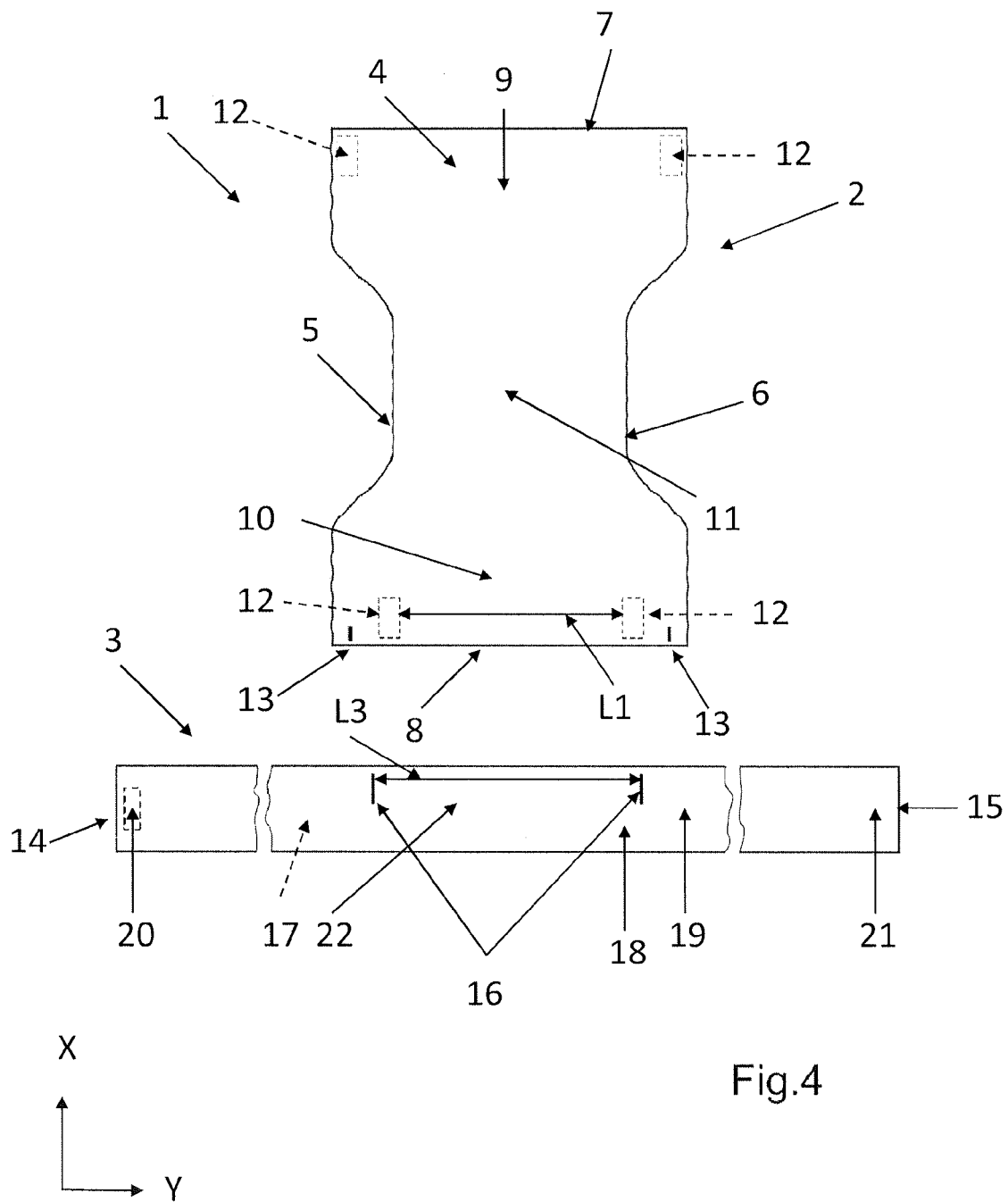

FIG. 4 schematically shows an article 1 including a chassis 2 and a belt 3 according to a fourth aspect. The difference between the chassis 2 described in connection to FIG. 4 and the chassis described in FIGS. 1-3 is that in FIG. 4 the first stretch markings 13 are placed outside the first fastening means 12. The same relationship between the first stretch markings 13 and the second stretch markings 16 as described in conjunction with the previous aspects apply. In FIG. 4, the first fastening means 12 located along the second lateral edge 8 are separated by a different distance L1 than the first fastening means 12 located along the first lateral edge 7. The distance between the first fastening means 12 located along the first and second lateral edge may be the same, or as shown in FIG. 4, different.

FIG. 4 does not show second elastic means on the chassis as described in connection to FIG. 3, but the chassis 2 in FIG. 4 could be equipped with such second elastic means in the way described in connection to FIG. 3.

Figure 5:
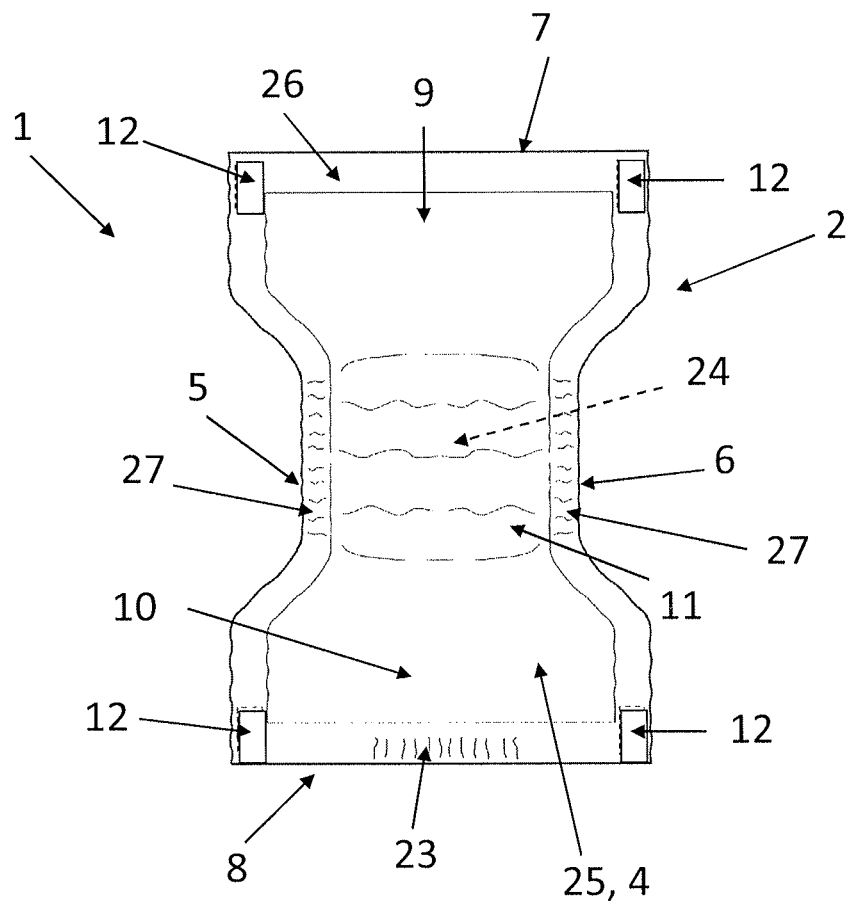

FIG. 5 schematically shows a chassis 2 according to a fifth aspect. In this aspect, the chassis 2 includes an absorbent core 24 placed between a top sheet 25 and a back sheet 26. The top sheet 25 is the layer which lies in contact with the wearer's body when the core is in use. As such, it should be soft, non-irritating and comfortable against the skin, and bodily fluid should be able to pass through it without hindrance. The top sheet 25 can consist of a nonwoven material, e.g. spunbond, meltblown, carded, hydroentangled, wetlaid etc. Suitable nonwoven materials can be composed of natural fibres, such as wood pulp or cotton fibres, manmade fibres, such as polyester, polyethylene, polypropylene, viscose etc or from a mixture of natural and manmade fibres. The top sheet 25 may further be composed of tow fibres, which may be bonded to each other in a bonding pattern. Further examples of materials suitable for top sheets are porous foams, apertured plastic films etc.

The back sheet 26 of the chassis 2 in this configuration is the layer which lies farthest from the wearer's body when the chassis 2 is in use. To protect the wearer's garments from soiling, it should be liquid-impermeable, but desirably gas-permeable (i.e. breathable) to allow air and vapour to pass in and out of the core so that the warm, damp conditions which can arise in the core are reduced. Typically, the back sheet 26 is of a liquid impervious material, such as a thin plastic film, e.g. a polyethylene or polypropylene film, a nonwoven material coated with a liquid impervious material, a hydrophobic nonwoven material, which resists liquid penetration or a laminate including plastic films and nonwoven materials. Examples of breathable back sheet materials are porous polymeric films, nonwoven laminates from spunbond and meltblown layers, laminates from porous polymeric films and nonwovens.

The absorbent core 24 of the chassis 2 in this configuration acts to receive and contain liquid and other bodily exudates and can be of any conventional kind. As such, it typically includes absorbent material. Examples of commonly-occurring absorbent materials are cellulosic fluff pulp, tissue layers, highly-absorbent polymers (so called superabsorbents), absorbent foam materials, absorbent nonwoven materials or the like. It is common to combine cellulosic fluff pulp with superabsorbents in an absorbent body. It is also common to have absorbent cores including layers of different material with different properties with respect to liquid receiving capacity, liquid distribution capacity and storage capacity. The thin absorbent cores, which are common in, for example, baby diapers and incontinence guards, often include a compressed mixed or layered structure of cellulosic fluff pulp and superabsorbent. The absorbent core 24 may include one or more layers which are designed to improve the handling of bodily waste. Such layers are designed to receive a large amount of liquid in a short space of time and distribute it. They may include so-called transfer, distribution, surge or acquisition layers, and are usually located between the top sheet 25 and the absorbent core 24. The top sheet 25 and back sheet 26 generally have a similar extension in the plane of the chassis, while the absorbent core 24 has an extension which is somewhat smaller. The top sheet 25 and back sheet 26 are joined to one another around the periphery of the absorbent core 24, so that the core is enclosed within the envelope formed by the top sheet 25 and the back sheet 26. The absorbent core 24 is at least located in the crotch portion 11 of the chassis, and may also extend somewhat into the front portion 9 and rear portion 10. The top sheet 25 and back sheet 26 may be joined to one another by any means common in the art, e.g., ultrasonic welding, thermal welding or gluing.

The chassis 2 may or may not include leg elastics. In FIG. 5, leg elastics 27 are schematically illustrated. The leg elastics 27 may be any suitable elastics known in the art.

The chassis 2 described in FIG. 3 could be used in any of the examples described in connection to FIGS. 1-4. The first stretch markings 13 could then be positioned accordingly and the chassis 2 could be equipped with second elastic means 23 as described in FIG. 3.

Figure 6:
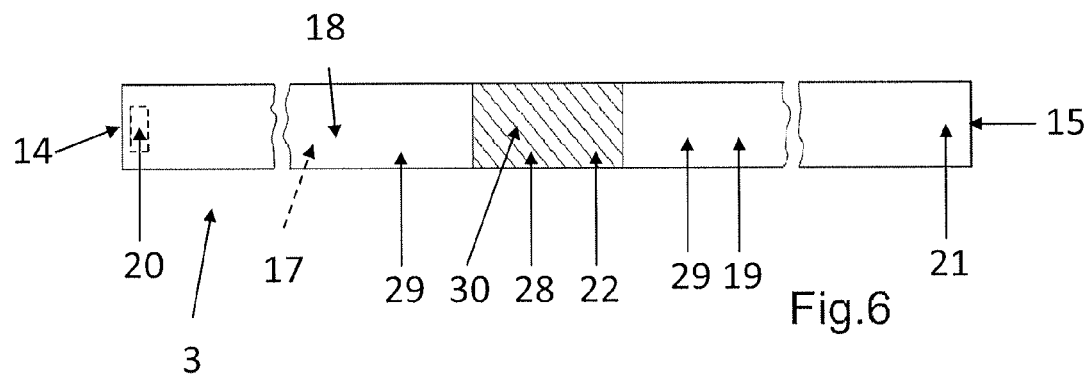
FIG. 6 schematically shows a belt according to a sixth aspect.

FIG. 6 schematically shows a belt 3 according to a sixth aspect. In FIG. 6, the belt 3 includes a first stretch zone 28 indicated by the shaded area. In FIG. 6, the belt 3 is elastic only in the first stretch zone 28. The remaining part of the belt 3 is essentially non-elastic. The first stretch zone 28 is thus sandwiched between two parts of essentially non-elastic members 29. It may of course be possible for a belt to have more than one stretch zone 28. The belt will then have discrete zones where the belt is elastic, where each zone is sandwiched between two essentially non-elastic members. The first stretch zone 28 may include a coloured region 30. The coloured region 30 may include ink added to the outer surface 18 of the belt 3 which faces away from the user's body. The belt 3 shown in FIG. 6 may be used together with any of the configurations of chassis 2 described in conjunction with FIGS. 1-5 above. The outer boundaries of the first stretch zone 28 then functions in the same way as the second stretch markings 16 of the belt 3 in FIGS. 1-4. In case the first stretch zone 28 does not include a coloured region the outer boundaries of the first stretch zone 28 may be indicated by a marking of a sort similar to the second stretch markings in FIGS. 1-4.

Figure 7:
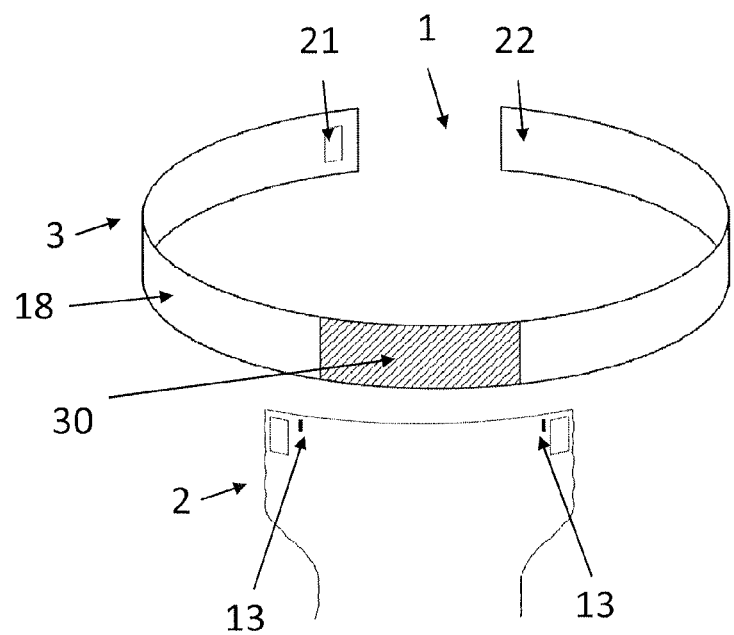
FIG. 7 schematically shows an article including a chassis and a belt prior to attachment of the chassis to the belt.

FIG. 7 schematically shows a chassis 2 and belt 3 prior to attachment of the chassis 2 to the belt 3. In FIG. 7, the belt 3 is curved to schematically indicate a suitable shape to put around the waist of a wearer. During use, the belt 3 is of course closed using the third and fourth fastening means 20, 21. The belt 3 includes a coloured region 30 on the outer surface 18 of the belt 3 that faces away from the wearer. The coloured region 30 marks out the stretch zone 28 described in FIG. 6. In FIG. 7, the belt 3 is in a stretched state as it is prepared to be put around the waist of a wearer. The position of the chassis 2 relative to the belt 3 is shown with the chassis 2 being placed at a distance from the belt 3 in FIG. 6 for simplicity. In reality, the chassis 2 would be placed on the belt 3. In the FIG. 7, first stretch markings 13 are placed outside of the coloured region 30.

In all examples described in connection to FIGS. 1-7, it is described with only one pair of first stretch markings 13. However, in all examples it could be possible to have a chassis including a number of pairs of first stretch markings with different distances between each pair. For example, one first pair of first stretch markings could be spaced with a first length and a second pair of first stretch markings could be spaced with a second length being greater than the first length. The first pair of first stretch markings could then be used together with the second stretch markings for a thinner user and the second pair for a larger user, since the belt stretches less for the thin user and more for the larger user. In a further example, the belt may include one first pair of second stretch markings spaced with a first length and a second pair of second stretch markings spaced with a second length being greater than the first length. The first pair of second stretch markings could then be used together with the first stretch markings for a thinner user and the second pair for a larger user, since the belt stretches less for the thin user and more for the larger user. In yet another example, both the chassis and the belt may include several pairs of stretch markings that could be matched to each other dependent on, for example, size of user, size of chassis and type of chassis.

As will be realised, the embodiments of the invention are capable of modification in various obvious respects, all without departing from the scope of the appended claims. Accordingly, the drawings and the description thereto are to be regarded as illustrative in nature, and not restrictive. For instance, the first stretch markings can be placed anywhere along either or both of the front portion and rear portion of the chassis. The second stretch markings of the belt can be adjusted to suit different sizes of waists of users.

The invention claimed is:

1. A wearable article comprising a chassis and a belt, the belt being separate from the chassis and arranged to be placed around the waist of a wearer,
   wherein the belt comprises an inner surface facing the user during use, an outer surface facing away from the user during use, and first elastic, which allows the belt to stretch during use in a lateral direction,
   wherein the chassis has longitudinal sides and lateral sides and is divided into a front portion, a rear portion and a crotch portion located between the front portion and the rear portion in a longitudinal direction, the chassis comprises at least a first layer of a conformable material for the user,
   wherein the front portion and/or the rear portion of the chassis comprises a pair of first fasteners arranged adjacent the longitudinal sides and being separated by a first distance,
   wherein the chassis is detachably attachable to the outer surface of the belt by the first fasteners, and the outer surface comprising corresponding second fasteners,
   wherein the chassis comprises a pair of first stretch markings directly or indirectly marking the position of the pair of first fasteners and being related to the first distance and wherein the belt comprises a pair of second stretch markings marking out a second distance when the belt is in a relaxed state, the distance between the first stretch markings being greater than the second distance in the relaxed state, and a predetermined third distance when the belt is in a stretched state, and
   wherein the first stretch markings are intended to, be positioned in conjunction with the second stretch markings or within the second distance for allowing the chassis to be attached to the belt via the first fasteners and allowing the belt to be stretched into the third distance without jeopardizing the fastening of the first fasteners.

2. The wearable article according to claim 1, wherein the first stretch markings are positioned in conjunction with the first fasteners.

3. The wearable article according to claim 1, wherein the distance between the first stretch markings is greater than the second distance in the relaxed state and wherein the distance between the first stretch markings is essentially equal to or greater than the third distance in the stretched state.

4. The wearable article according to claim 1, wherein the second distance is dependent on the stretchability of the first elastic.

5. The wearable article according to claim 1, wherein the chassis comprises second elastic, wherein the first stretch markings marks out a fourth distance when the chassis is in a predetermined maximum stretched state, and wherein the fourth distance is essentially equal to or greater than the third distance in the stretched state.

6. The wearable article according to claim 1, wherein the third distance relates to a predetermined maximum stretch value of the belt in the stretched state.

7. The wearable article according to claim 1, wherein the belt comprises a first stretch zone, and wherein the distance between the outer boundaries of the first stretch zone, when elongated to its maximum, is less than or equal to the distance between the first stretch markings in the chassis, when the chassis is stretched out to its maximum.

8. The wearable article according to claim 7, wherein the distance between the outer boundaries of the first stretch zone on the belt, when elongated to a maximum stretch of the belt, is less than or equal to the distance between the first stretch markings on the chassis, when the chassis is stretched out to 90% of its maximum.

9. The wearable article according to claim 7, wherein the first stretch zone of the belt comprises elastic sandwiched between two essentially non-elastic members.

10. The wearable article according to claim 7, wherein the first stretch zone on the belt comprises a coloured region.

11. The wearable article according to claim 7, wherein the first stretch zone on the belt comprises ink added to the outer surface of the material which is placed away from the user's body.

12. The wearable article according to claim 1, wherein the chassis and/or the belt is made from a washable material.

13. The wearable article according to claim 1, wherein chassis comprises a top sheet, a back sheet and an absorbent core placed in-between the top sheet and the back sheet.

14. The wearable article according to claim 1, wherein the first fasteners comprise loop material and the second fasteners comprise hook material, or vice versa.

15. The wearable article according to claim 1, wherein the entire belt is elasticated.

16. The wearable article according to claim 1, wherein the first stretch markings on the chassis comprise two transversal extending marks separated from each other.

* * * * *